United States Patent [19]

Soloway et al.

[11] Patent Number: 5,171,849
[45] Date of Patent: Dec. 15, 1992

[54] 2' AND 3' CARBORANYL URIDINES AND THEIR DIETHYL ETHER ADDUCTS

[75] Inventors: Albert H. Soloway, Worthington; Rolf F. Barth; Abul K. Anisuzzaman, both of Columbus, all of Ohio; Fazlul Alam, Anaheim, Calif.; Werner Tjarks, Columbus, Ohio

[73] Assignee: The Ohio State University Research Foundation, Columbus, Ohio

[21] Appl. No.: 688,121

[22] Filed: Apr. 19, 1991

[51] Int. Cl.[5] .................... C07H 19/00; C07H 23/00
[52] U.S. Cl. .......................... 536/23; 536/50
[58] Field of Search .............. 536/23, 50; 514/49, 514/50, 64

[56] References Cited

U.S. PATENT DOCUMENTS 5,021,572 6/1991 Gabel ............................. 544/229
5,116,980 5/1992 Gabel ............................. 544/229

OTHER PUBLICATIONS

Barth et al., Cancer Research, vol. 50, pp. 1061–1070, Feb. 15, 1990.
Barth et al., "Boron Neutron Capture Therapy for Cancer", Scientific American, vol. 262, No. 10, 100–107, Oct. 1990.
Mishima et al., "Treatment of Malignant Melanoma by Selective Thermal Neutron Capture Therapy Using Melanoma-Seeking Compound", The Journal of Investigative Dermatology, vol. 92, No. 5, Supplement, May 1989, 321S–325S.
Heying et al., A New Series of Organoboranes. I. Carboranes from the Reaction of Decaborane with Acetylenic Compounds, Inorg. Chem. 1963, vol. 2, No. 6, 1089.
Barth et al., "Determination of Boron in Tissues and Cells Using Direct-Current Plasma Atomic Emission Spectroscopy", Anal. Chem., 1991, vol. 63, pp. 890–893.

Primary Examiner—Johnnie R. Brown
Assistant Examiner—J. Oliver Wilson
Attorney, Agent, or Firm—Frank H. Foster

[57] ABSTRACT

There is disclosed a process for preparing carboranyl uridine nucleoside compounds and their diethyl ether adducts, which exhibit a tenfold increase in boron content over prior art boron containing nucleoside compounds. Said carboranyl uridine nucleoside compounds exhibit enhanced lipophilicity and hydrophilic properties adequate to enable solvation in aqueous media for subsequent incorporation of said compounds in methods for boron neutron capture therapy in mammalian tumor cells.

3 Claims, No Drawings

2' AND 3' CARBORANYL URIDINES AND THEIR DIETHYL ETHER ADDUCTS

This invention herein was made with government support under Grant RO1 CA 41288 awarded by the National Cancer Institute and Grants DE-FG02-90ER60972 and BNL 464374 awarded by the Department of Energy. The government has certain rights in this invention.

TECHNICAL FIELD

This invention relates to certain 2' and 3' carboranyl uridines and their usage. More particularly, the invention concerns the just-mentioned carboranyl uridines and contemplates that these carboranyl uridines will be useful capture compounds in boron neutron capture therapy (BNCT).

BACKGROUND ART

Boron neutron capture therapy (BNCT) for the treatment of mammalian tumors (e.g. cancerous tumor cells) is based on the nuclear reaction between thermal neutrons and boron-10 to yield alpha particles and lithium-7 nuclei:

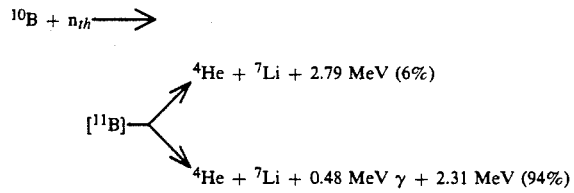

The high linear energy transfer (LET) alpha particles released in this nuclear reaction have a range in tissue of about 10 μm, approximately equal to the diameter of a single cell. Their destructive effect is, therefore, highly localized to boron-loaded tissue. A key requirement of BNCT is the selective delivery of an adequate concentration of boron-10 to tumors (15–30 μg $^{10}$B/g tumor). The lack of boron compounds with the requisite biological properties has been a major limitation for the clinical use of BNCT. Boronated analogues of compounds that are known to localize in various tumors (amino acids, thiouracils, chlorpromazine, nucleosides, antibodies, etc.) have been the focus of compound development in this area. The rationale for the synthesis of boron-containing nucleosides is that such structures would be conserved by rapidly proliferating tumor cells and phosphorylated by cellular kinases to mononucleotides. These may persist "locked-in" within the tumor cell or possibly be converted to the active precursors of nucleic acids, the di- and triphosphate forms.

A recent review article on BNCT can be found in *Cancer Research*, 50, 1061–1070, Feb. 15, 1990, "Boron Neutron Capture Therapy of Cancer", Rolf F. Barth, Albert H. Soloway and Ralph G. Fairchild. Another more recent review is in *Scientific American*, October 1990, Vol. 262, No. 10, pp. 100–107, "Boron Neutron Capture Therapy for Cancer", Rolf F. Barth et al. This latest review on pages 106–107 in its penultimate and ultimate columns speaks of BNCT treatments reported by Yutaka Mishima and his associates, including working with Duroc pigs and injecting a boron compound around a skin-level melanoma, following with exposure to thermal neutrons, and after several months noting that the melanomas began to shrink and eventually disappeared (apparently also reported in *The Journal of Investigative Dermatology*, Vol. 92, No. 5, Supplement, May 1989, 321S–325S). The "Scientific American" review in the paragraph bridging pages 106–107 also reports achieving through BNCT of a cure of primary melanomas on two patients.

The first mentioned review (i.e. *Cancer Research*, supra) on page 1063 in Table 1 tabulates some current boron compounds either being used or potentially useful as capture agents for BNCT therapy. Included in that tabulation is a 5-borono-2'-deoxy uridine, which compound contains a single B atom linked to its nuclei acid moiety of the nucleoside.

OBJECTS OF THE INVENTION

Since prior BNCT-used nucleosides generally contained a single boron atom inserted into or linked or attached to the purine or pyrimidine base moiety thereof, an object of this invention was to incorporate or link a carboranyl moiety to the sugar moiety of the nucleoside and desirable a carboranyl moiety providing a significant increase in boron content so as to enhance subsequent reaction between neutrons and boron-10.

Other objects and advantages will be apparent to one of skill in the art from the disclosure and claims which follow.

BRIEF DISCLOSURE OF INVENTION

The invention includes BNCT capture compounds which incorporate a carboranyl moiety into or on the carbohydrate portion of the nucleoside. These carboranyl nucleosides are believed to be novel and also to possess: about (1) a tenfold increase in boron content compared to prior art single boron atom nucleosides; (2) enhanced lipophilicity for cellular penetration due to the carborane moiety; (3) possible cellular entrapment and retention properties in proliferating tumor cells due to the action of kinases; and (4) a retained capacity when incorporated into an oligonucleotide to hybridize strongly with RNA and DNA sequences since the base component would be naturally-occurring.

The invention includes a novel carboranyl uridine of the structure

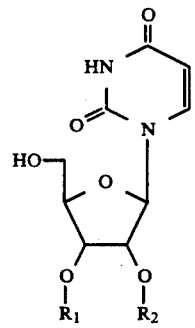

wherein one of $R_1$ and $R_2$ is —H and the other of $R_1$ and $R_2$ is

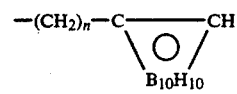

in which n is the integer 1 or 2, and the diethyl ether adducts of the carboranyl uridine. Encompassed by these carboranyl nucleosides are:
2'-O-(o-carboran-1-ylmethyl)uridine;
3'-O-(o-carboran-1-ylmethyl)uridine;
2'-O-(o-carboran-1-ylethyl)uridine;
3'-O-(o-carboran-1-ylethyl)uridine;
and their diethyl ether adducts.

The invention also includes a method of boron neutron capture therapy of mammalian tumor cells comprising:

a) introducing a diether adduct of or carboranyl uridine of the structure

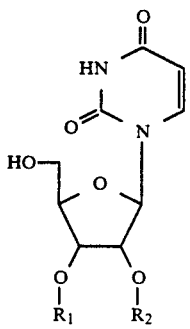

wherein one of $R_1$ and $R_2$ is —H and the other of $R_1$ and $R_2$ is

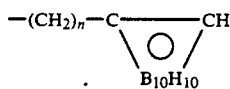

with n being 1 or 2 in a manner and for a time effective to be retained by the tumor cells; and b) radiating with neutrons of said diether adduct of or said carboranyl uridine retained in said tumor cells.

In describing the preferred invention, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected or terms similar thereto are often used. They are not limited to direct connection but include connection through other elements where such connection is recognized as being equivalent by those skilled in the art.

DETAILED DESCRIPTION

The invention's carboranyl uridine compounds are defined and tabulated earlier herein. The preferred compound for contemplated BNCT employment is the diether adduct of 2'-O-(o-carboran-1-ylmethyl)-uridine, which advantageously possesses hydrophilic properties adequate to enable solvation in aqueous media for subsequent incorporation in and neutron capture within the mammalian tumor cell.

In general, the invention's carboranyl uridine compounds are prepared by a synthesis method which proceeds through: the initial alkylation of 2',3'-O-(dibutylstannylene)uridine with 3-bromopropyne or 4-bromobutyne-1 (depending on the end product sought—note examples which follow). This utilized alkylation reagent is of the structure $Br(CH_2)C≡CH$ wherein n is 1 or 2. The alkylation reaction proceeds readily in dimethyl formamide (DMF) with heating for several hours, e.g. 100° C. for four hours, and then DMF is removed by vacuum evaporation and the residue processed by silica gel column chromatography using chloroform: methanol (about 20:1 parts by volume) as the eluent. The produced alkylation product is a mixture of the alkylation of the 2'- and 3'-O- positions on the carbohydrate portion of the uridine. This mixture then is acetylated, conveniently with acetic anhydride in pyridine at about room temperature for between 12 to 24 hours. The acetylated mixture then is subjected to separation and purification by chromatographic means, such as a column of silica gel and an eluant which is a hexane:ethylacetate mixture generally 2:1 parts by volume, respectively. The resulting separated mixture's components of 3',5'-di-O-acetyl-2'-O-(-3-alkynl)uridine and 2',5'-di-O-acetyl-3'-O-(-3-alkynl)uridine then each separately is reacted with bis(acetonitrile)decaborane in an organic solvent (e.g. toluene) under a nitrogen atmosphere at an elevated temperature for several hours, e.g. 85°–90° C. for three hours, to yield the di-O-acetylated derivative of the to-be-produced desired carboranyl uridine. This di-O-acetylated derivative subsequently is quantitatively deacetylated by catalytic amounts of sodium methoxide in methanol at a low temperature, such as about 4° C. for about four hours Passage of the deacetylated compound in methanol through a cation exchange resin removes sodium and provides the desired carboranyl uridine in methanol. Subjecting the desired carboranyl uridine in methanol to reduced pressure removes methanol and provides a smaller volume, which upon addition of diethyl ether thereto provides the desirable diethyl ether adduct of the desired carboranyl uridine. Additional details and procedural teachings will be apparent from the specific examples which follow shortly.

It is contemplated that the invention's herein carboranyl uridines and their diethyl ether adducts will be useful for boron neutron capture therapy (BNCT) of mammalian tumors. The tumors contemplated as subjectable to this BNCT may be malignant or benign. The contemplated mammals having such mammalian malignant and benign tumors include: horses, cows, pigs, dogs, cats, guinea pigs, hamsters, rats, mice, humans, etc. From the BNCT reviews cited supra, it will be apparent, or at least determinable without undue experimentation, from the techniques for administration of other capture compounds, various suitable dosages, administration techniques, neutron radiation levels and times and techniques, which also will be useful for the herein taught carboranyl uridines contemplated employed as capture compounds for BNCT. For example, and contemplated as preferred embodiments are the diethyl ether adducts in aqueous media, especially the diethyl ether adduct of 2'-O-(o-carboran-1-ylmethyl)uridine, in water or in slightly saline water and administered preferably by injection, preferably intravenously, or into the tumor mass per se or through intracarotid infusion as well as other known administrative techniques and methods. If eradication of the tumor mass is sought and contemplated, there are administered those dosage amounts of the carboranyl uridines effective to provide tumor cell uptake and retention of a B-10 content in the equivalent amount as taught in the art for B-10 in art-used capture compounds for providing eradication of cells. It is contemplated that lesser dosage amounts than those requisite for eradication also will be of some utility in alleviation of tumor effects, if only in aesthetic appearance as of a diminished tumor size, or even of a hindering of the growth of the tumor, following the neutron radiation in BNCT, and thus in the case of BNCT of a mammalian malignant tumor of possible prolonged life duration.

Additional details and elements of the invention will be apparent from the illustration specific examples which follow.

EXAMPLE A

A mixture of uridine, obtained from Aldrich Chemical Co., Milwaukee, Wis., (1.94 g), dibutyltin oxide (2 g) and methanol (200 ml) was heated under reflux for two hours. Methanol was removed under reduced pressure and the solid residue was dried under vacuum to provide 2',3'-O-(Dibutylstannylene)uridine, having Structure I, illustrated below.

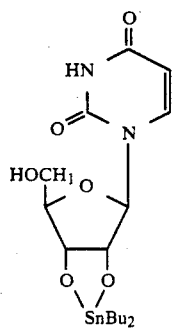

Structure I

2',3'-O-(Dibutylstannylene)uridine thus obtained was dissolved in dimethyl formamide (DMF) (40 ml) and heated at 100° C. for four hours with propargy bromide (1.2 g). DMF was removed by evaporation under reduced pressure and the residue was processed by column chromatography on silica gel 60 (obtained from EM Science, Gibbstown, N.J.) using chloroform:methanol (20:1 parts by volume) as the eluant. A mixture (1 g) of 2'-O-(3-propynyl)uridine and 3'-O-(3-propynyl)uridine was obtained having the respective Structures II and III, illustrated below

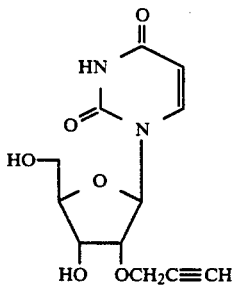

Structure II

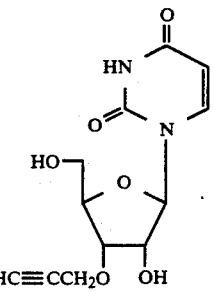

Structure III

A mixture of (2 g) of 2'-O-(3-propynyl)uridine and 3'-O-(3-propynyl)uridine was reacted with acetic anhydride (5 ml) in the presence of pyridine (10 ml) at 25° C. for 18 hours. Pyridine and the excess of acetic anhydride were removed by evaporation under reduced pressure. The residue was partitioned between dichloromethane and water. The dichloromethane layer was dried over anhydrous sodium sulfate, the solvent layer was removed and evaporated to a residue. This mixture was purified by column chromatography by the use of silica gel 60 with a hexane:ethyl acetate (2:1 parts by volume) solvent mixture as the eluant. Pure 3',5'-di-O-acetyl-2'-O-(-3-propynyl)uridine (2.5 g), Structure IV, and pure 2',5'-di-O-acetyl-3'-O(-3-propynyl)uridine (1.7 g) Structure V, were obtained. Each of their structures were confirmed by NMR, mass spectrometry and microanalysis. Structures IV and V are illustrated below.

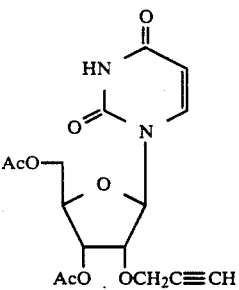

Structure IV

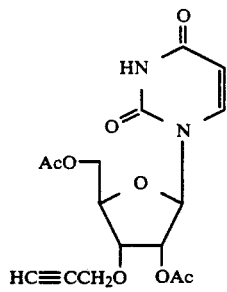

Structure V

A mixture of 3',5'-di-O-acetyl-2'-O-(-3-propynyl)uridine (2 g), bis(acetonitrile)decaborane (1.9 g), prepared according to the Heying et al. teachings (Inorg. Chem. 1963, 2, 1089), and toluene (100 ml) were heated together under a nitrogen atmosphere for three hours at 85° C. The solvent was removed and the residue was extracted with ethyl ether. The evaporation of the ether extract gave a product which was purified by column chromatography on silica gel 60. A mixture of hexane:ethyl acetate (2:1 parts by volume) was used as the eluant to give 3',5'-di-O-acetyl-2-O-(-o-carboran-1-ylmethyl)uridine (1.3 g), Structure VI (illustrated below).

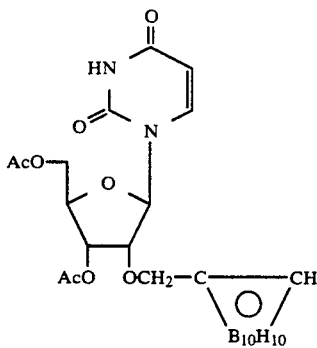

Structure VI

3',5'- di-O-acetyl-2-O-(-o-carboran-1-ylmethyl)uridine (500 mg), Structure VI, was quantitatively deacetylated by catalytic amounts of sodium methoxide in methanol at 4° C. for 20 hours; sodium was removed with cation exchange resin and the solution concentrated under reduced pressure to a small volume, which contained 2'-O-(-o-carboran-1-ylmethyl)uridine, Structure VII (illustrated below)

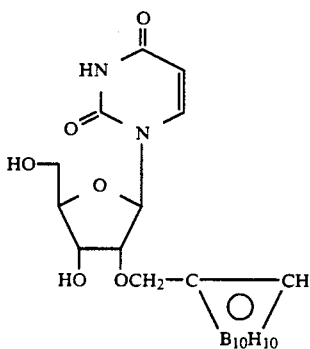

Structure VII

Addition of diethyl ether yielded crystalline 2'-O-(o-carboran-1-ylmethyl)uridine (Structure VII) as an ether adduct, m.p. 136°–137° C. $[\alpha]^D{}_{25}+4.6°$ (cl, MeOH). The IR spectrum exhibits a strong adsorption at 2575 cm$^{-1}$, characteristic of B-H stretch and the carbonyl absorption at 1695 cm$^1$. The proton NMR spectrum (in CD$_3$OD, 250 MHz; σ in ppm downfield from TMS, coupling constant in Hz) exhibits the following peaks: 3.67, 3.80 (ABq, H-5'a, H-5'b; J$_{5'a,5'b}$12.3; J$_{4',5'a}$2.7; J$_{4',5'b}$2.3); 4.64 (bs, carborane C-H); 5.60 (d, H-5; J$_{5,6}$8.1); 5.77 (d, H-1'; J$_{1',2'}$2.7); 8.00 (d, H-6). The peaks due to diethyl ether in the solvated Structure VII occur as a triplet at 1.11 and a quartet at 3.42. The mass spectra (FAB) shows the M'+H) peak at m/z 401 as part of the carborane isotopic cluster. Elemental analysis (Cl$_6$H$_{34}$O$_7$N$_2$B$_{10}$·0.8Et$_2$O): Theo: C, 39.71; H, 7.02; N, 6.09. Found: C, 39.47; H, 7.09; N, 5.89.

EXAMPLE B

A mixture of 2',5'-di-O-acetyl-3-O-(-o-carboran-1-ylmethyl)uridine (2 g) (prepared according to the teachings in EXAMPLE A), Structure V, bis(acetonitrile) decaborane (1.9 g), prepared according to the Heying et al. teachings (Inorg. Chem., 1963, 2, 1089) and toluene (100 ml) were heated together under a nitrogen atmosphere for three hours at 85° C. The solvent was removed and the residue was extracted with ethyl ether. The evaporation of the ether extract gave a product which was purified by column chromatography on silica gel 60. A mixture of hexane:ethyl acetate (2:1 parts by volume) was used as the eluant to give 2',5'-di-O-acetyl-3-O-(-o-carboran-1-ylmethyl)uridine, Structure VIII (illustrated below).

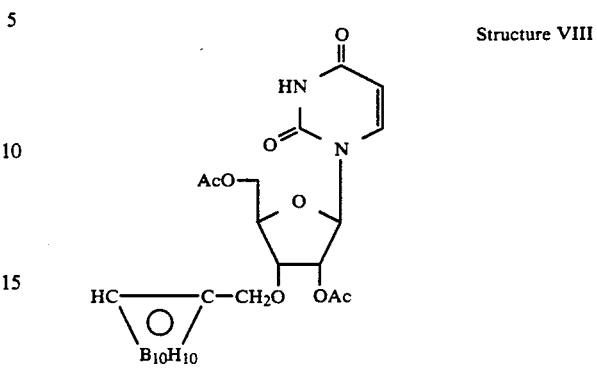

Structure VIII

2',5'-di-O-acetyl-3-O-(-o-carboran-1-ylmethyl)uridine (500 mg), Structure VIII, was quantitatively deacetylated by catalytic amounts of sodium methoxide in methanol at 4° C. for 20 hours; sodium was removed with cation exchange resin and the solution concentrated under reduced pressure to a small volume, which contained 3'-O-(-o-carboran-1-ylmethyl)uridine, Structure IX (illustrated below).

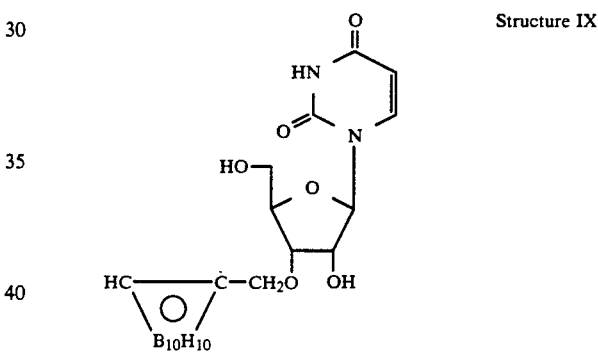

Structure IX

Addition of diethyl ether yielded crystalline 3'-O-(-o-carboran-1-ylmethyl)uridine (Structure IX) as an ether adduct. Ether is removed at elevated temperature (∼100° C.) and reduced pressure to give a compound free of ether: m.p. 202°–204° C. Elemental analysis (C$_{16}$H$_{34}$O$_7$N$_2$B$_{10}$) Theo: C, 35.99; H, 6.04; N, 7.00. Found: C, 36.19; H, 5.92; N, 6.78. IR spectrum, proton NMR spectrum and mass spectra (FAB) confirmed that the named compound of Structure IX was obtained.

EXAMPLE C

When EXAMPLE A is repeated except in place of propargyl bromide (i.e. 3-bromopropyne) there is used 4-bromobutyne-1 (the next higher homologue in this bromoalkyne series) there is obtained 2'-O-(o-carboran-1-ylethyl)uridine, which upon addition of diethyl ether yields an adduct.

EXAMPLE D

When 2',5'-di-O-acetyl-3-O(-o-carboran-1-ylethyl) uridine is prepared according to and as in EXAMPLE C and then used in place of the next lower homologue of 2',5'-di-O-acetyl-3-O(-o-carboran-1-ylmethyl)uridine to repeat EXAMPLE B, there is obtained 3'-O-(-o-carboran-1-ylethyl)uridine, which upon the addition of diethyl ether yields an adduct.

EXAMPLE E

To illustrate the uptake, and retention of the various carbonyl uridines prepared as taught in the preceding illustrative EXAMPLES A–D, there was evaluated 2'-O-(-o-carboran-1-ylmethyl)uridine, Structure VII (as prepared according to EXAMPLE A) as its ether adduct, in F98 glioma cells. For comparison therewith, a clinically-used $Na_2B_{12}H_{11}SH$ compound was employed and also evaluated.

To demonstrate whether there was cellular uptake and retention, the following procedure was used. Semi-confluent F98 glioma cells were incubated with the compound for 16 hours and after two washings with serum free media, the cells were trypsinized, washed twice again and aliquots were analyzed for boron by Direct Current Plasma (DCP) Atomic Emission Spectroscopy. For the boron analyses there was used the following instrumentation and sample preparation for analysis:

INSTRUMENTATION

A Spectraspan VB Direct Current Plasma-Atomic Emission Spectrometer, (Model #DCP-AES, Applied Research Laboratories, Brea, Calif.) was used for the boron determinations. This instrument combines a high resolution spectrometer with a high resolution Echelle grating and prism. The plasma source is argon gas heated to a temperature of 6000°–7000° K. The instrument settings used for analysis were: wave length 249.773 nm, argon flow 7L/min sleeve 50 psi, ceramic nebulizer 20 psi, entrance slits 50–300 μm, as predetermined by the manufacturer. The viewing height was 1 nm between the arms of the "V" of the inverted "Y" configuration created by the three electrodes. The liquid uptake rate was approximately 2 mL/min. The operating power, once the plasma was established, was ~40 V in the jet power supply with a 7 amp constant current output. With the operating parameters used no background correction was needed. Integration times and gain had been optimized by the manufacturer and were preset in the computer software. These particular parameters are not user alterable.

SAMPLE PREPARATION FOR ANALYSIS

One to 2 mL of concentrated sulfuric acid, which was adequate for up to 1 g of tissue or cells, were added to 150×16 mm Pyrex culture tubes, and these were placed in a mineral oil bath, heated to 100° C. in an exhaust hood and stirred intermittently for one hour. Since no interference with the boron signal was found with the sulfuric acid-hydrogen peroxide cocktail, the amount of sulfuric acid used in digestion was determined by the ease of digestion for a particular sample, rather than by any specific ratio of sample weight to acid volume. The amount and type of tissue were critical factors for successful digestion. If the amount of tissue or cells approached 1 gram or more, there was more chance for overheating and loss of sample by bubbling. If sample size was small (<200 mg) there was more flexibility in terms of acid volume and digestion time.

The results for cellular uptake and retention (i.e. persistence studies) for the illustrative evaluated carboranyl uridine of this invention compared to the clinically-used $Na_2B_{12}H_{11}SH$ compound are shown in the following TABLE 1.

TABLE 1

| Compound | Boron Conc. in Incubating Media g/ml | F98 Glioma Cells Boron Conc. /g 16 hrs incubation | Persistence Studies | | |
|---|---|---|---|---|---|
| | | | 12 hrs | 24 hrs B/g | 48 hrs |
| $Na_2B_{12}H_{11}SH$ | 14.6 | 4.3 | 3.1+ | .4+ | * |
| $Na_2B_{12}H_{11}SH$ | 58.0 | 7.2 | 2.8+ | .8+ | * |
| $Na_2B_{12}H_{11}SH$ | 116.0 | 26.7 | 3.4+ | 1.8+ | * |
| Carboranyl Uridine | 13.5 | 88.9 | 23.9 | 19.3 | 10.5 |
| Carboranyl Uridine | 40.5 | 98.2 | 24.1 | 22.0 | 12.7 |

*Not measured
+These approximate the blank value for cells - the average DCP reading being 1.3 (range .4–3.0)

The results, as shown in TABLE 1, demonstrate significantly greater incorporation of the evaluated invention's carboranyl uridine compared with the clinically-used compound. While it is not fully known yet, and the invention is not to be so limited as to the specific basis for the superior incorporation, the greater lipophilicity of the carboranyl uridine in comparison to the mercaptopolyhedral borane anion may account, at least in part, for the greater incorporation.

Of importance, once a boron-containing compound has been taken up by a cell, regardless of the biochemical mechanism involved in the take-up or capture, is whether or not it is retained or is washed out into its environmental surroundings (e.g. growth or incubating media). Accordingly, in order to determine whether such cellular persistence occurred, cells which had demonstrated compound uptake were resuspended in boron-free media and incubated for 12, 24, and 48 hours. Aliquots of cells were then analyzed for boron content and these are also presented in TABLE 1. It is apparent from these preliminary results that the invention's carboranyl uridine persists for appreciable times once it is incorporated into F98 glioma cells and this is in marked contrast with $Na_2B_{12}H_{11}SH$, which is rapidly removed, attaining background levels within 6–12 hours.

EXAMPLE F

As additional examples of Cellular Uptake of Carboranyl Uridines (CBU) of the invention:

1) One mg of CBU is solubilized in a 2% solution of β-cyclodextrin. Varying amounts of the CBU of the invention are then added to Dulbecco's Minimal Essential Medium supplemented with 10% fetal bovine serum.

2) Tumor and normal cells growing in T75 tissue culture flasks (Corning, Corning, N.Y.), are cultured in the presence of CBU containing medium for 16 hours following which the medium is removed, the cells resuspended in 10 ml of Phosphate Buffered Saline (PBS), transferred to a 15 ml conical centrifuge tube, and sedimented at 3,000 rpm. Washing is repeated three times and then the cell pellet is transferred to a 15 ml boron free glass test tube.

3) Cells are solubilized by adding 0.5 ml of concentrated sulfuric acid, heating them at 100° C. in an oil bath for 15 minutes, and then decolorized by adding a few drops of 70% hydrogen peroxide. The solubilized cells are then diluted with deionized water to a final volume of 2 ml. 4) Boron concentrations are determined by means of direct current plasma-atomic emission spectroscopy, as described earlier and also in great detail by Barth et al *Analytical Chemistry,* 63:890–893, 1991.

Upon proceeding as just described in this EXAMPLE F, for each of the following CBU of the invention, the diethyl ether adduct of 2'-O-(o-carboran-1-ylmethyl)uridine, the diethyl ether adduct of 3'-O-(o-carboran-1-ylmethyl)uridine, the diethyl ether adduct of 2'-O-(o-carboran-1-ylethyl)uridine, and diethyl ether adduct of 3'-O-(o-carboran-1-ylethyl)uridine, there will be noted a significant uptake for each CBU in the tumor cells and a very much smaller uptake, very minimal, for each CBU in the normal cells. Additionally, upon conducting of persistence studies, conducted substantially as described in previous EXAMPLE F, there will be noted a long lasting persistence (i.e. retention of a larger amount of the earlier retained B take-up) of the B content in the tumor cells.

EXAMPLE G

This example describes Cell Survival Studies Following Exposure to Carboranyl Uridine and Neutro Irradiation by proceeding as follows:

1) Tumor and normal cells in suspension are placed in 3 ml screw top plastic tubes containing Dulbecco's MEM containing varying concentrations of the various CBUs of the invention.

2) Cells are then irradiated by exposing them to a beam of thermal neutrons of varying fluences (neutrons/centimeter$^2$/second).

3) The irradiated cells are then plated out in 120 mm Petri dishes at varying concentrations, serum supplemented Dulbecco's MEM is added, and they are incubated at 37° C. in a humidified incubator containing 5% $CO_2$ for 7–10 days.

4) Cultures are then terminated, cells fixed with 2 ml of buffered formalin, washed, dried, and then stained with 2% crystal violet.

5) Colonies are enumerated with an automated colony counters (Artek) and the surviving fraction (S.F.S.) are calculated.

6) The tumoricidal effect is determined by comparing S.F.S. of non-irradiated and irradiated cells in the presence or absence of the various CBUs of the invention.

For each of the cells subjected to at least some of the varied concentrations of the various CBUs of the invention and then subsequently irradiated there will be found a calculated smaller number of surviving fractions (S.F.S.) in comparison to the S.F.S. found for control cells not subjected to the various CBUs of the invention and non-irradiated.

The preceding disclosure is intended to be illustrative and descriptive of the invention made, but the true scope and full extent of the scope of the invention is believed to be only apparent from the claims, which follow, when read in light of the preceding disclosure.

We claim:

1. A carboranyl uridine of the structure

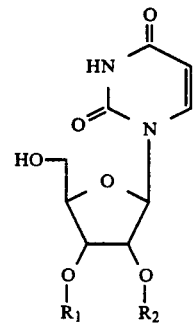

wherein one of $R_1$ and $R_2$ is —H and the other of $R_1$ and $R_2$ is

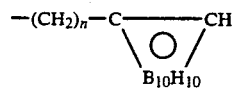

in which n is the integer 1 or 2, and the diethyl ether adducts of the carboranyl uridine.

2. The carboranyl uridine of claim 1 which is the diethyl ether adduct of 2'-O-(o-carboran-1-ylmethyl)uridine.

3. The carboranyl uridine of claim 1 which is the diethyl ether adduct of 3'-O-(o-carboran-1-ylmethyl)uridine.

* * * * *

UNITED STATES PATENT AND TRADEMARK OFFICE
CERTIFICATE OF CORRECTION

PATENT NO.   :   5,171,849
DATED        :   December 15, 1992
INVENTOR(S)  :   Albert H. Soloway et al.

It is certified that error appears in the above-identified patent and that said Letters Patent is hereby corrected as shown below:

```
Column 2, line 12, "nuclei" should read --nucleic--.
Column 3, line 67, "Br(CH2)C≡CH" should read
--Br(CH2)nC≡CH--.  Column 4, line 26, before "Passage"
insert a period mark --.--.  Column 5, line 35, "propargy"
should read --propargyl--.  Column 11, line 22, "Neutro"
should read --Neutron--.
```

Signed and Sealed this

Second Day of November, 1993

Attest:

BRUCE LEHMAN

Attesting Officer

Commissioner of Patents and Trademarks